US009898582B2

(12) United States Patent
Reddy

(10) Patent No.: US 9,898,582 B2
(45) Date of Patent: Feb. 20, 2018

(54) SYSTEM AND METHOD FOR ANALYZING AN IMPACT OF A SOFTWARE CODE MIGRATION

(71) Applicant: SYNTEL, INC., Troy, MI (US)

(72) Inventor: Murlidhar Reddy, Maharashtra (IN)

(73) Assignee: Syntel, Inc., Troy, MI (US)

(*) Notice: Subject to any disclaimer, the term of this patent is extended or adjusted under 35 U.S.C. 154(b) by 0 days.

(21) Appl. No.: 14/305,994

(22) Filed: Jun. 16, 2014

(65) Prior Publication Data
US 2014/0372978 A1 Dec. 18, 2014

Related U.S. Application Data

(60) Provisional application No. 61/834,908, filed on Jun. 14, 2013.

(51) Int. Cl.
G06F 9/44 (2006.01)
G06F 9/45 (2006.01)
G06F 9/445 (2006.01)
G06F 19/00 (2018.01)
G06Q 50/22 (2018.01)

(52) U.S. Cl.
CPC ............ G06F 19/328 (2013.01); G06F 8/30 (2013.01); G06F 8/70 (2013.01); G06Q 50/22 (2013.01); G06F 19/322 (2013.01)

(58) Field of Classification Search
CPC .... G06F 8/30–8/75; G06F 8/433; G06F 8/20; G06F 19/30–19/3487; G06F 11/3604; G06Q 50/22
See application file for complete search history.

(56) References Cited

U.S. PATENT DOCUMENTS

| 4,558,413 | A  | 12/1985 | Schmidt et al. |
| 6,493,871 | B1 | 12/2002 | McGuire et al. |
| 7,233,938 | B2 | 6/2007 | Carus et al. |
| 7,437,302 | B2 | 10/2008 | Haskell et al. |
| 7,546,595 | B1 | 6/2009 | Wickham et al. |

(Continued)

OTHER PUBLICATIONS

Cognizant, Preparing and Implementing a Comprehensive ICD-10 Testing Strategy, 2012, pp. 1-6.*

(Continued)

Primary Examiner — Thuy Dao
Assistant Examiner — Mongbao Nguyen
(74) Attorney, Agent, or Firm — Dykema Gossett PLLC

(57) ABSTRACT

A system for analyzing an impact of a software migration on a codebase includes a data management module to receive user-selected input of a codebase that supports international classification of diseases, ninth revision (ICD-9) codes and that contains a plurality of lines of source code and a plurality of codebase components, to receive user selection of at least one search string and to analyze the codebase using the at least one search string to identify at least one of each impacted line of the plurality of lines of source code in the codebase and each impacted codebase component, each impacted line of source code and each impacted codebase component requiring modification in order to support migration from ICD-9 codes to international classification of diseases, tenth revision (ICD-10) codes, and produce at least one report of a result of the analysis of the codebase.

17 Claims, 13 Drawing Sheets

(56) References Cited

U.S. PATENT DOCUMENTS

| | | | |
|---|---|---|---|
| 7,861,239 B2 | 12/2010 | Mayfield et al. | |
| 8,015,136 B1* | 9/2011 | Baker | G06F 19/322 |
| | | | 706/45 |
| 8,265,952 B1* | 9/2012 | Smith | G06Q 50/22 |
| | | | 705/2 |
| 8,370,799 B2 | 2/2013 | Nir-Buchbinder et al. | |
| 8,510,240 B2* | 8/2013 | Patrao | G06F 19/3487 |
| | | | 706/14 |
| 2003/0191665 A1 | 10/2003 | Fitzgerald et al. | |
| 2005/0137912 A1 | 6/2005 | Rao et al. | |
| 2008/0195999 A1* | 8/2008 | Cohen et al. | 717/100 |
| 2008/0201611 A1* | 8/2008 | Bassin | G06F 11/3604 |
| | | | 714/37 |
| 2009/0138453 A1* | 5/2009 | Jee | G06F 17/30067 |
| 2009/0150181 A1 | 6/2009 | Gejdos et al. | |
| 2009/0164252 A1 | 6/2009 | Morris et al. | |
| 2009/0265189 A1* | 10/2009 | Bartholomew, III | G06Q 10/10 |
| | | | 705/3 |
| 2009/0288073 A1* | 11/2009 | Gosalia | G06F 8/33 |
| | | | 717/141 |
| 2010/0094657 A1* | 4/2010 | Stern et al. | 705/3 |
| 2010/0165690 A1* | 7/2010 | Gupta | G11C 15/04 |
| | | | 365/49.11 |
| 2010/0198799 A1 | 8/2010 | Krishnan et al. | |
| 2010/0241469 A1* | 9/2010 | Weigert | G06F 11/3604 |
| | | | 717/124 |
| 2011/0066425 A1* | 3/2011 | Hudgins | G06F 17/278 |
| | | | 704/10 |
| 2011/0107318 A1* | 5/2011 | Kumar | G06F 11/3688 |
| | | | 717/168 |
| 2011/0184946 A1* | 7/2011 | Hennum | G06F 17/30672 |
| | | | 707/728 |
| 2012/0078979 A1* | 3/2012 | Ghimire | G06F 17/3064 |
| | | | 707/805 |
| 2012/0089964 A1* | 4/2012 | Sawano | 717/124 |
| 2012/0110016 A1* | 5/2012 | Phillips | G06F 19/322 |
| | | | 707/780 |
| 2012/0254083 A1* | 10/2012 | Patrao | G06F 19/3487 |
| | | | 706/14 |
| 2012/0311426 A1* | 12/2012 | Desai et al. | 715/227 |
| 2013/0006653 A1* | 1/2013 | Mills | G06Q 50/22 |
| | | | 705/2 |
| 2013/0035947 A1* | 2/2013 | Sundararam | G06Q 50/22 |
| | | | 705/2 |
| 2013/0073301 A1* | 3/2013 | Rao | G06Q 40/08 |
| | | | 705/2 |
| 2013/0144651 A1* | 6/2013 | Rao | 705/3 |
| 2013/0185094 A1* | 7/2013 | Mukerji | G06Q 10/00 |
| | | | 705/3 |
| 2013/0227524 A1* | 8/2013 | Im | G06F 8/75 |
| | | | 717/121 |
| 2013/0227533 A1 | 8/2013 | Tonkin et al. | |
| 2013/0253947 A1* | 9/2013 | Drabo | G06F 19/322 |
| | | | 705/3 |
| 2014/0109067 A1* | 4/2014 | Flicker | G06F 8/423 |
| | | | 717/142 |
| 2014/0136495 A1* | 5/2014 | Kottaram | G06Q 50/22 |
| | | | 707/695 |
| 2014/0136559 A1* | 5/2014 | Kottaram | G06Q 50/22 |
| | | | 707/756 |
| 2014/0173574 A1* | 6/2014 | Schmidt | G06F 8/427 |
| | | | 717/143 |
| 2014/0181128 A1* | 6/2014 | Riskin | G06F 17/30684 |
| | | | 707/756 |
| 2014/0331202 A1* | 11/2014 | Fukuda | G06F 8/75 |
| | | | 717/123 |
| 2016/0110505 A1* | 4/2016 | Symanski | G06F 19/322 |
| | | | 705/3 |

OTHER PUBLICATIONS

Anita Hazlewood, ICD-9 CM to ICD-10 CM: Implementation Issues and Challenges, 2003, pp. 1-7. http://library.ahima.org/doc?oid=59978#.Wc1_6f7rvDA.*

Donna Pickett, Understanding the Impact of the Difference in ICD-9-CM and ICD-10-CM and its potential impact on data analysis, 2012, pp. 105-112. https://www.cdc.gov/nchs/ppt/nchs2012/li-01_pickett.pdf.*

Oracle, Successful Data Migration, an Oracle White Paper, 2011, pp. 1-15. http://www.oracle.com/technetwork/middleware/oedq/successful-data-migration-wp-1555708.pdf.*

Joseph C Nichols, ICD-10 DRG Impacts at the Hospital Level, 2012, pp. 1-12. http://healthdataconsulting.com/_wp/wp-content/uploads/2012/06/DRGImpacts.pdf.*

Stein, Brian D., et al,. "The Validity of International Classification of Diseases, Ninth Revision, Clinical Modification Diagnosis Codes for Identifying Patients Hospitalized for COPD Exacerbations." CHEST Journal 141.1 (2012), pp. 87-93.

McDonald, Clement J., et al. "Open Source Software in Medical Informatics—Why, How and What." International Journal of Medical Informatics 69.2 (2003), pp. 175-184.

Ayewah, Nathaniel, et al. "Evaluating Static Analysis Defect Warnings on Production Software", Proceedings of the 7th ACM SIGPLAN-SIGSOFT Workshop on Program Analysis for Software Tools and Engineering, ACM, (2007), pp. 1-7.

* cited by examiner

EXCEL

| A | B | C | D | E | F | G | H | I | J |
|---|---|---|---|---|---|---|---|---|---|
| LIB. NAME | COMP. NAME | COMP. TYPE | FILE NAME | IT R # | LN # | CODE | VAR NAME | NXT LVL VAR. | IMPCTD CATGY |
| | | | XYZ.txt | 1 | 11 | C MOVEL DATA APP#L2 | DATA | APP#L | TECH |
| | | | XYZ.txt | 1 | 85 | C MOVE DATA @ACODE2 | DATA | @ACODE | TECH |
| | | | XYZ.txt | 1 | 89 | CALL DATA WIND02 | DATA | | TECH |
| | | | YZX.txt | 2 | 103 | C PARM @APPLCOD | @APPL | | TECH |
| | | | ZXY.txt | 2 | 92 | C MOVE @ACODES9APPL | @ACODE | APPLCD | TECH |
| | | | ZXY.txt | 2 | 115 | C MOVELS9APPL @APPL2 | @APPL | | TECH |
| | | | BBT.txt | 3 | 47 | I 1 2 APPLCD | APPLCD | | TECH |
| | | | BBT.txt | 3 | 54 | KFLD APPLCD | APPLCD | | TECH |

DETAIL | SUMMARY | CROSSREF | MISSING COMP | INSTR 1100
1102 1104 1106 1108 1110

FIG. 11

SYSTEM AND METHOD FOR ANALYZING AN IMPACT OF A SOFTWARE CODE MIGRATION

CROSS-REFERENCE TO RELATED APPLICATION

This application claims the benefit of, and priority to, U.S. patent application Ser. No. 61/834,908, filed Jun. 14, 2013, the disclosure of which is incorporated herein by reference in its entirety.

FIELD OF THE INVENTION

This disclosure relates generally to a computerized system and method for healthcare-related data, and more specifically to a system and method for analyzing an impact of a software code migration such as from ICD-9 to ICD-10 code sets.

BACKGROUND

Healthcare legislation specifies procedures for communicating information within the healthcare industry. For example, Title II (Administrative Simplification provisions) of the Health Insurance Portability and Accountability Act of 1996 ("HIPAA") required the Department of Health and Human Services to establish national standards for electronic health care transactions and national identifiers for providers, health plans, and employers.

On Jan. 1, 2012, an updated version of the healthcare transactions standard, HIPAA 5010, replaced version 4010A1, the current set of standards. Among various changes in this update, HIPAA 5010 mandates changes to the International Classification of Diseases ("ICD"), which is a nomenclature for the classification of diseases, injuries, and other medical conditions. More specifically, HIPAA 5010 requires healthcare payers and providers to transition from the current International Classification of Diseases, 9th Revision, Clinical Modification ("ICD-9") to a 10th revision ("ICD-10"). This transition is referred to herein as the "ICD-10 migration" and, at present, all healthcare stakeholders (e.g., providers, payers, and employers), must make this transition by Oct. 1, 2015.

ICD-10 codes exhibit fundamental differences as compared with ICD-9 codes. For example, the form and information conveyed in ICD-10 codes is different than that of the ICD-9 codes. More specifically, ICD-9 codes contain three to five digits beginning with either a number or a letter, with a decimal point placed after the third digit, and the ICD-9 book indicates the level of specificity for each code. ICD-10 codes, on the other hand, are seven digits in length. The first three digits of the ICD-10 codes are similar to the ICD-9 codes, with a decimal point after the third digit. However, the digits that follow the decimal point have different, specific meanings. For medical and surgical procedures, for example, the digits that follow are specific to body part, surgical approach, and other qualifiers needed for billing. Similarly, the ICD-10 codes that represent diagnosis codes also have seven digits.

The first three digits of ICD-10 codes are similar to the ICD-9 code, but the additional digits add specificity to the code such as laterality, chronic versus acute, and so on. Another significant difference between the ICD-9 and ICD-10 code sets is the number of codes. More specifically, ICD-9 includes just over 14,000 diagnosis codes and almost 4,000 procedural codes. In contrast, ICD-10 contains over 68,000 diagnosis codes (clinical modification codes) and over 72,000 procedural codes. Due to such fundamental differences, mapping or translation from the ICD-9 code set to the ICD-10 code set presents challenges to ICD-10 migration. For example, while there are some one-to-one correspondences between ICD-9 and ICD-10 codes, there are also one-to-many, many-to-one and many-to-many correspondences and, in some cases, no correspondence at all. Accordingly, ICD-10 migration will undoubtedly affect many aspects of information collection, reporting requirements, billing and payment systems, potentially resulting in benefit, financial and clinical variations.

SUMMARY

The present invention may comprise one or more of the features recited in the attached claims, and/or one or more of the following features and combinations thereof. In one aspect, a system for analyzing an impact of a software migration on a codebase may comprise a data management module to receive user-selected input of a codebase that supports international classification of diseases, ninth revision (ICD-9) codes and that contains a plurality of lines of source code and a plurality of codebase components, and to receive at least one search string, a codebase analysis module to analyze the codebase using the at least one search string to identify at least one of each impacted line of the plurality of lines of source code in the codebase and each impacted codebase component, each impacted line of source code and each impacted codebase component requiring modification in order to support migration from ICD-9 codes to international classification of diseases, tenth revision (ICD-10) codes, and a report module to produce at least one report of a result of the analysis of the codebase by the codebase analysis module.

In another aspect, a method for analyzing an impact of a software migration on a codebase may comprise receiving user-selected input of a codebase that supports international classification of diseases, ninth revision (ICD-9) codes and that contains a plurality of lines of source code and a plurality of codebase components, receiving user selection of at least one search string, receiving user selection of an analysis initiation, and in response to receipt of the analysis initiation, analyzing the codebase using the at least one search string to identify at least one of each impacted line of the plurality of lines of source code in the codebase and each impacted codebase component, each impacted line of source code and each impacted codebase component requiring modification in order to support migration from ICD-9 codes to international classification of diseases, tenth revision (ICD-10) codes, and producing at least one report of a result of the analysis of the codebase.

In yet another aspect, a computer program product may comprise a non-transitory computer readable medium having instructions stored thereon which, when executed by at least one processor, cause the processor to receive user-selected input of a codebase that supports international classification of diseases, ninth revision (ICD-9) codes and that contains a plurality of lines of source code and a plurality of codebase components, receive user selection of at least one search string, receive user selection of an analysis initiation, and in response to receipt of the analysis initiation, analyze the codebase using the at least one search string to identify at least one of each impacted line of the plurality of lines of source code in the codebase and each impacted codebase component, each impacted line of source code and each impacted codebase component requiring modification in order to support migration from ICD-9 codes to international classification of diseases, tenth revision (ICD-10) codes, and produce at least one report of a result of the analysis of the codebase.

BRIEF DESCRIPTION OF THE DRAWINGS

This disclosure is illustrated by way of example and not by way of limitation in the accompanying FIGS. Where considered appropriate, reference labels have been repeated among the FIG. s to indicate corresponding or analogous elements.

FIG. 11 is an example report exported by the impact analysis sub-module illustrated in FIG. 2.

DETAILED DESCRIPTION OF THE DRAWINGS

Figure 1:
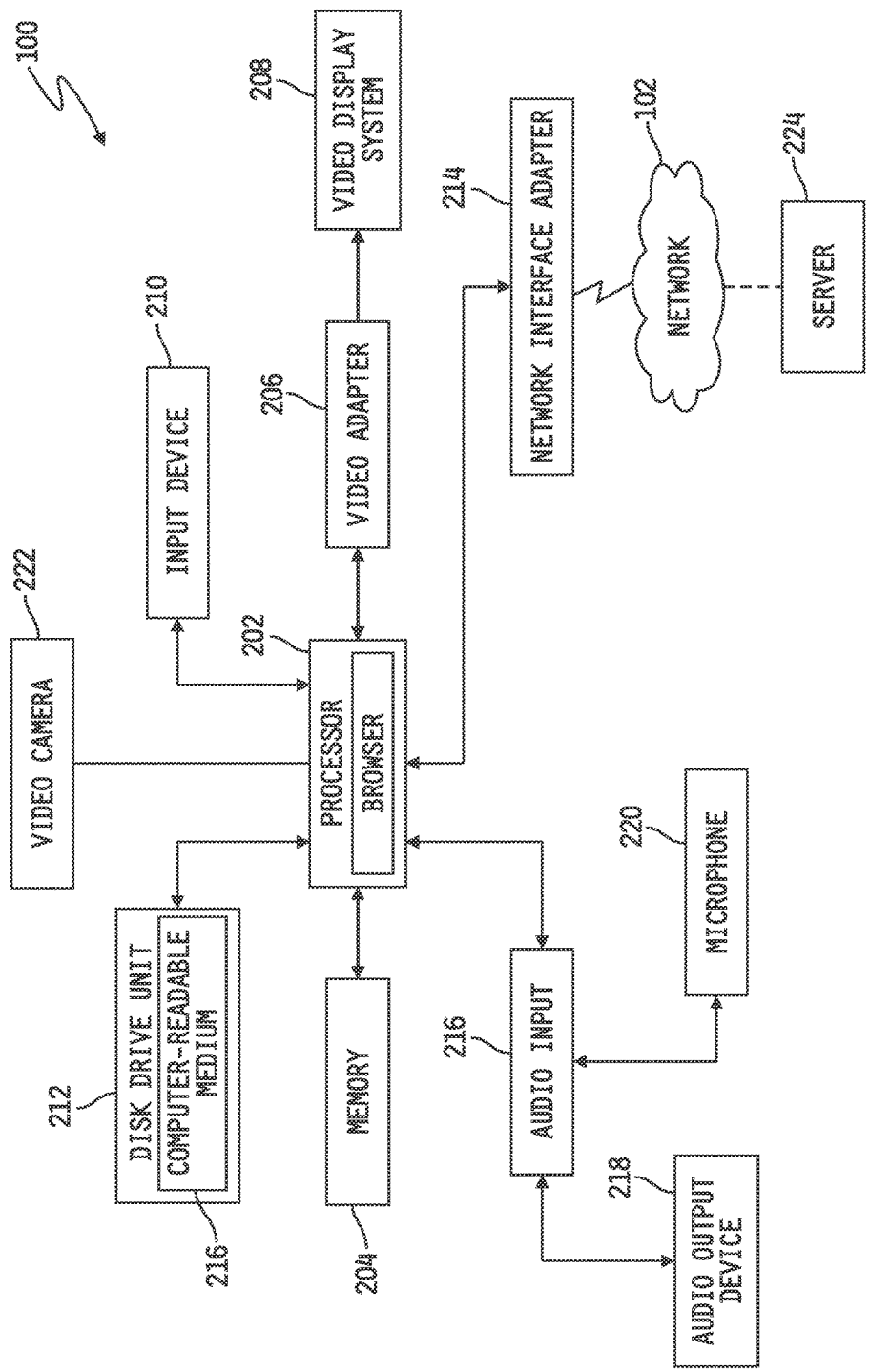
FIG. 1 is a simplified block diagram of an embodiment of a computerized system that may be programmed with a set of instructions to perform any one or more of the functions, processes and methods discussed herein.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

This application relates to the following applications all filed on even date herewith, the disclosures of which are incorporated herein by reference in their entirety; U.S. patent application Ser. No. 14/306,060, entitled System and Method for Providing Mapping Between Different Disease Classification Codes, U.S. patent application Ser. No. 14/306,208, entitled System and Method for Ensuring Medical Benefit Claim Payment Neutrality Between Different Disease Classification Codes, U.S. patent application Ser. No. 14/306,026, entitled System and Method for Automatically Modifying Source Code to Accommodate a Software Code Migration, and U.S. patent application Ser. No. 14/306,077, entitled System and Method for Validating Medical Claim Data.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases may or may not necessarily refer to the same embodiment. Further, when a particular feature, structure, process, process step or characteristic is described in connection with an embodiment, it is submitted that it is within the knowledge of one skilled in the art to effect such feature, structure, process, process step or characteristic in connection with other embodiments whether or not explicitly described. Further still, it is contemplated that any single feature, structure, process, process step or characteristic disclosed herein may be combined with any one or more other disclosed feature, structure, process, process step or characteristic, whether or not explicitly described, and that no limitations on the types and/or number of such combinations should therefore be inferred.

Embodiments of this disclosure may be implemented in hardware, firmware, software, or any combination thereof. Embodiments of this disclosure implemented in a computer system may include one or more bus-based interconnects between components and/or one or more point-to-point interconnects between components. Embodiments of this disclosure may also be implemented as instructions stored on one or more machine-readable media, which may be read and executed by one or more processors. A machine-readable medium may be embodied as any device or physical structure for storing or transmitting information in a form readable by a machine (e.g., a computing device). For example, a machine-readable medium may be embodied as any one or combination of read only memory (ROM); random access memory (RAM); magnetic disk storage media; optical storage media; flash memory devices; and others.

Referring now to FIG. 1, an embodiment is shown of a system 100 for analyzing an impact of a software code migration, e.g., from an ICD-9 code set to an ICD-10 code set. Although a migration from ICD-9 to ICD-10 is discussed herein for purposes of example, this disclosure is not intended to be limited to migration from ICD-9 to ICD-10, but encompasses migration from any one medical classification system to another medical classification system. The computing device 100 may be a personal computer, a tablet computer, a personal digital assistant ("FDA"), a media player, a cellular telephone, or any machine capable of executing a set of instructions (sequential or otherwise) that specify actions to be taken. The system 100 according to embodiments of the present disclosure may include a processor 202 (e.g., a central processing unit ("CPU")), a memory 204, a video adapter 206 that drives a video display system 208 (e.g., a liquid crystal display ("LCD"), a cathode ray tube ("CRT"), a touch screen), an input device 210 (e.g., a keyboard, mouse, touch screen display, etc.) for the user to interact with the program (e.g., browser), a disk drive unit 212, a network interface adapter 214, an audio in/out jack 216 that allows audio to be outputted/received by an audio output device 218 (e.g., speaker, headphones) and microphone 220, respectively. Although a combined audio in/out jack 216 is shown for purposes of example, one skilled in the art should appreciate that separate devices may be provided for input and output of audio. It will be understood that that various embodiments of the computing device 100 may not always include all of these peripheral devices, and may instead include various subsets thereof. It will further be understood that the video display system 208 may, in some embodiments, be provided in the form of one or more conventional display monitors.

The disk drive unit 212 includes a computer-readable medium 216 on which may be stored a program code for a web browser with commonly installed plugin(s), such as Flash™ and/or Java™. In some cases, the browser may provide support for the emerging HTML5 WebRTC standard. Embodiments are also contemplated in which the browser could be on a mobile internet connected device, such as a phone or tablet, which has support for the emerging HTML5 WebRTC standard. In one embodiment, a custom application could be provided on an Internet connected mobile device. The term "computer-readable medium" shall be taken to include, but not be limited to, solid-state memories, optical media, flash memory, and magnetic media. Embodiments are contemplated in which the browser may run applications that are received from a server 224 over a network 102 via the network interface device 214 utilizing any one of a number of transfer protocols including but not limited to the hypertext transfer protocol ("HTTP") and file transfer protocol ("FTP"). The network 102 may be any type of packet-switched data network including but not limited to fiber optic, wired, and/or wireless communication capability in any of a plurality of protocols, such as TCP/IP, Ethernet, WAP, IEEE 802.11, or any other protocol.

Compliance with the above discussed migration from ICD-9 to ICD-10 code sets may impact the software and systems of health care providers and payers. Embodiments of the present disclosure are directed to a software code migration impact analysis tool that generally identifies impacted lines of source code in a codebase and impacted codebase components, i.e., each line of source code and each software component in the codebase that is impacted by the ICD-9 to ICD-10 migration. As used herein, the term "impacted line" in the context of a line of source code that is "impacted by" the ICD-9 to ICD-10 migration, is defined as a line of source code in a codebase that requires modification in order to support the ICD-9 to ICD-10 migration. Examples of modifications that may be required of an "impacted line" of source code in order for the modified codebase to support the ICD-9 to ICD-10 migration include, but are not limited to, (1) modifying an ICD-9 code with a mapping to at least one corresponding ICD-10 code, (2) modifying at least one data field length, (3) adding at least one data field, (4) renaming at least one data field, (5) modifying at least one data type, (6) modifying at least one logical expression in the line of source code, (7) adding at least one data declaration, and (8) adding at least one data movement instruction.

As also used herein, the term "codebase component" is defined in a conventional manner as the source code of a unit of a computer software program, file/table definition or job controlling language/procedure. Examples of codebase components include, but are not limited to, class libraries, class objects, web services, stored software procedures, COBOL programs, copybooks, Job Control Language (JCL) and the like. Examples of computer software items that are generally not considered codebase components include, but are not limited to, single statements and lines within a computer program source code, an executable file, a compiled source code and data records. The term "impacted component" as used in the context of a codebase component that is "impacted by" the ICD-9 to ICD-10 migration, is defined as a codebase component that requires modification in order to support the ICD-9 to ICD-10 migration.

Software source code used in current health care systems may be generically referred to herein as a "codebase." The impact of migration from ICD-9 to ICD-10 code sets in such source code is illustratively quantified with the software code migration impact analysis tool described in detail below by searching a codebase to identify all impacted lines of source code in the codebase and/or all impacted components in the codebase, and collecting the results of such a search in the form of various report files. The analysis carried out by the software code migration impact analysis tool may prove to be useful for conducting work estimates and assigning roadmaps for migrating existing healthcare system software applications from ICD-9 to ICD-10 compatible applications.

Figure 2:
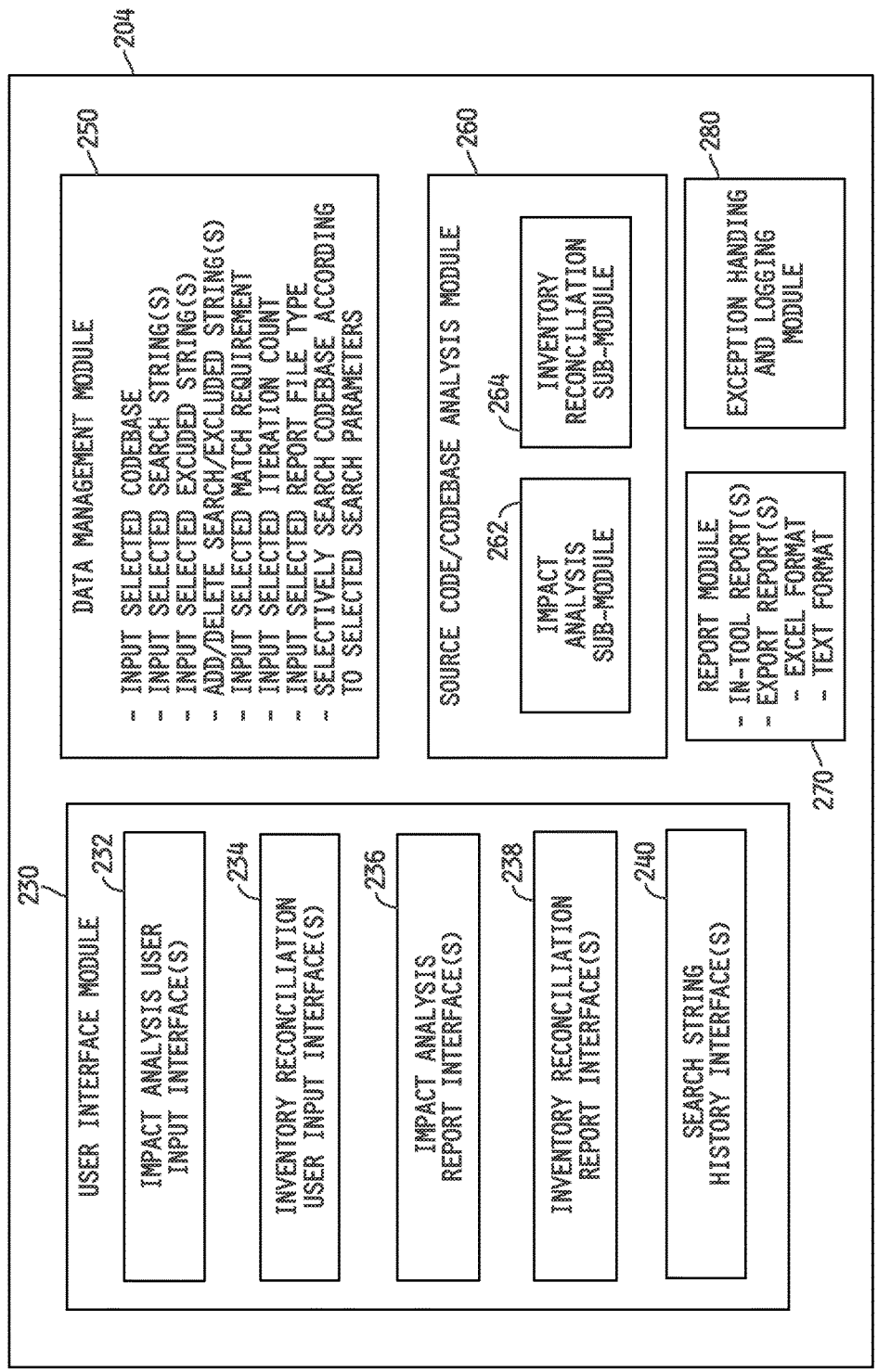
FIG. 2 is a simplified block diagram representation of a software code migration impact analysis tool executed by the system illustrated in FIG. 1.

Referring now to FIG. 2, a simplified block diagram is shown of a software environment of the system of FIG. 1. In the illustrated embodiment, the software code migration impact analysis tool is implemented in the form of instructions stored in the memory 204 of the system 100 and executable by the processor 202 to perform the functions described herein. Alternatively or additionally, the instructions may be stored in whole or in part on the computer-readable medium 216, and/or on the server 224 and accessed by the processor 202 via the network 102. Alternatively or additionally still, the server 224 may include one or more processors which execute the instructions, and input/output data may be exchanged between the processor 202 and the server 224 via the network 102. In any case, the software code migration impact analysis tool includes a user interface module 230, a data management module 250, a source code/codebase analysis module 260, a report module 270 and an exception handling and logging module 280.

The user interface module 230 includes a number of graphic user interfaces for receiving user input and for producing reports generated by the software code migration impact analysis tool. In the illustrated embodiment, for example, the user interface module 230 includes one or more impact analysis user input interfaces 232, one or more inventory reconciliation user input interfaces 234, one or more impact analysis report interfaces 236, one or more inventory reconciliation report interfaces 238, and one or more search string history interfaces 240. It will be understood that while some embodiments may include all such interfaces, other embodiments may include various subsets of such interfaces. Examples of some such graphic user interfaces are illustrated in one or more of FIGS. 4-14.

The data management module 250 manages the input of information to, and user control of, the software code migration impact analysis tool. For example, the data management module 250 illustratively manages the input to the tool of a codebase selected by the user, of one or more search strings selected by the user, of one or more excluded search strings selected by the user, of one or more search strings to be added or deleted as selected by the user, of an iteration count selected by the user and of one or more report types selected by the user. Optionally, as will be described in greater detail hereinafter, some embodiments of the data management module 250 may further manage the input to the tool of a search string match requirement and/or of one or more types of reports selected by the user. The data management module 250 further initiates searching of the codebase by the tool in response to user input.

The source code/codebase analysis module 260 (which may at times be referred to herein as a "source code analysis module" or a "codebase analysis module") illustratively includes an impact analysis sub-module 262 and an inventory reconciliation sub-module 264. As briefly described above, and as will be described in greater detail below, the impact analysis sub-module 262 is generally operable to search a selected codebase to identify all impacted lines of source code in the codebase, i.e., those which require modification in order to support the ICD-9 to ICD-10 migration, and to collect the results of such a search in the form of various report files. As will also be described in greater detail below, the inventory reconciliation sub-module 264 is generally operable to search a selected codebase to identify all impacted codebase components, i.e., those which require modification in order to support the ICD-9 to ICD-10 migration, and to collect the results in the form of various report files. In the embodiments illustrated herein, the impact analysis sub-module 262 and the inventory reconciliation sub-module 264 are separate from each other and individually selectable by the user such that the tool may be configured by the user to search a selected codebase using only the impact analysis sub-module 262, using only the inventory reconciliation sub-module 264 or both of the sub-modules 262 and 264.

The report module 270 illustratively operates to produce a number of different in-tool reports detailing the results of searches conducted by the impact analysis sub-module 262 and the inventory reconciliation sub-module 264. In some embodiments, the report module 270 further includes a report exportation feature which exports the results of any such search into a pre-configured file of selectable format. The exception handling and logging module 280 operates to handle data access and logic exceptions, and to log such exceptions into a log file contained in memory.

Figure 3:
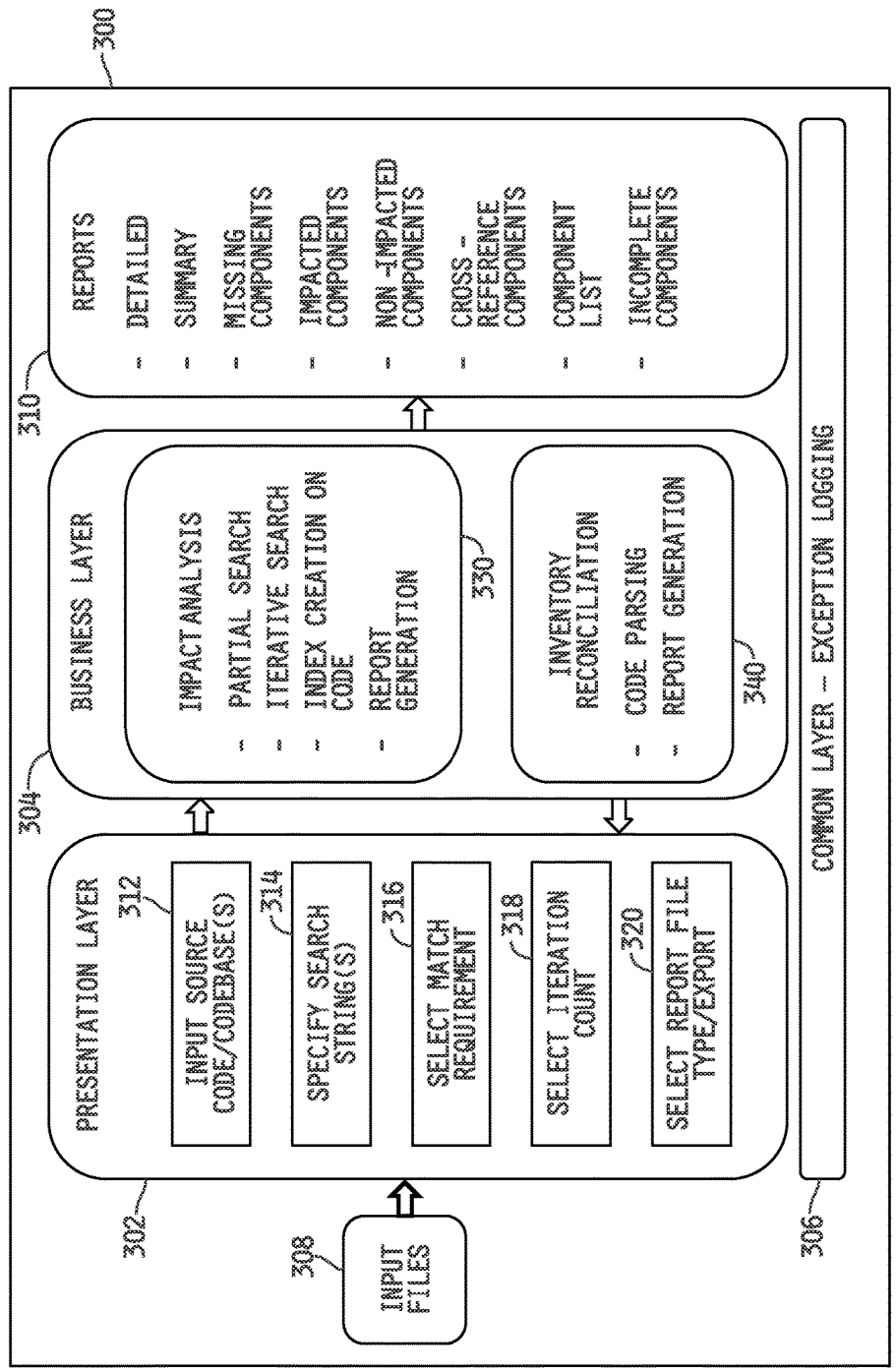
FIG. 3 is a simplified block diagram depicting an example architecture of the software code migration impact analysis tool.

FIG. 3 is a block diagram illustrating an example architecture 300 of the software code migration impact analysis tool. The architecture 300 includes, but is not limited to a presentation layer 302, a business layer 304 and a common layer 306. The presentation layer 302 provides an interface 312 for the user to input one or more data files 308 in the form of source code or a codebase corresponding to a healthcare system software application that supports at least the ICD-9 code set. The tool illustratively supports analysis of source code or codebases provided in various different programming languages, examples of which include, but are not limited to, C#, VB, .NET, SQL, Oracle, DTS, Mainframe, AS400, etc.

The presentation layer 302 further provides an interface 314 for the user to specify one or more search strings, an interface 318 for the user to selection a search iteration count and an interface 320 for the user to select one or more in-tool report files. In some embodiments, the presentation layer 302 may further provide an interface 316 for the user to select a matching requirement for searches conducted by the tool, and in some embodiments the interface 320 may further allow the user to export one or more report files in a selectable report format.

The business layer 304 contains the components which implement the business logic and rules responsible for the functionality of the impact analysis system. These components include, but are not limited to: an impact analysis component 330 responsible for conducting various searches and generating search result reports, and an inventory reconciliation component 340 likewise responsible for conducting various searches and generating search result reports. The common layer 306 is responsible for the exception and error handling common to the above discussed layers.

The impact analysis component 330 and the inventory reconciliation component 340 are each illustratively operable to generate a number of different reports 310 detailing the results of searches carried out thereby. Examples of such reports 310 may include, but are not limited to, detailed reports, summary reports, missing component reports, impacted component reports, non-impacted component reports, cross-reference component reports, component list reports and incomplete component reports.

Figure 4:
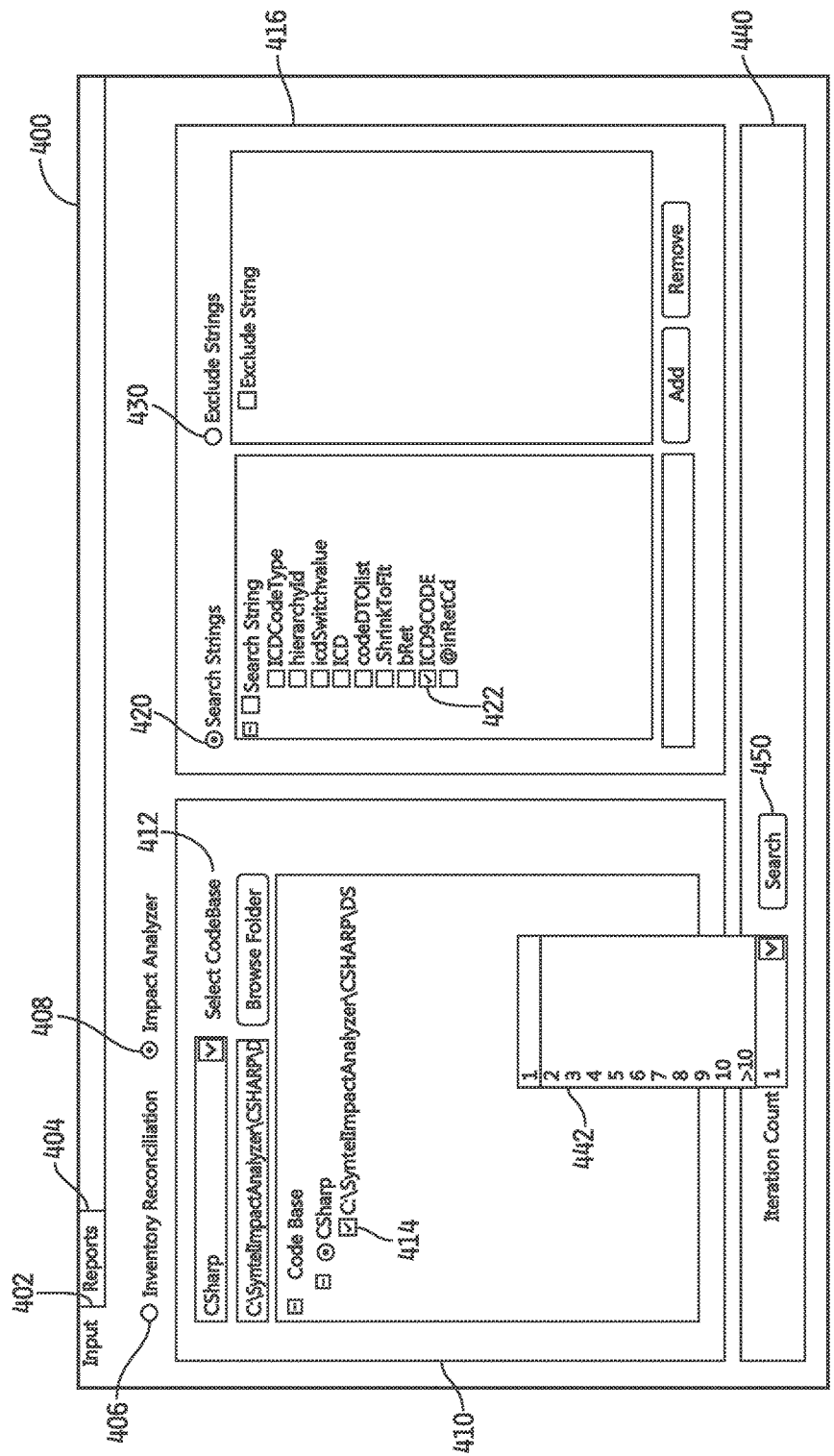
FIG. 4 is an example screen shot illustrating a process for inputting information into the system of FIG. 1 for processing by the impact analysis sub-module illustrated in FIG. 2.

Upon loading the tool, as shown in FIG. 4, a user is presented with a main menu screen 400, which illustratively includes a data input tab 402 and a reports tab 404. In the screen shot of FIG. 4, the data input tab 402 is selected from which the user may, in one embodiment, select either an inventory reconciliation search/analysis or an impact analysis search/analysis via on-screen radio buttons 406 and 408 respectively. In some embodiments, the user may, within tab 402, select both an inventory reconciliation search/analysis and an impact analysis search/analysis. In any case, in the screen shot of FIG. 4, the impact analysis radio button 408 is selected, which produces on-screen user input interfaces 410, 416 and 440. The user input interface 410 includes features which allow a user to identify one or more codebases on which the tool is to operate, and further includes a "select codebase" button or feature 412 that allows the user to select any number of codebases 414 for analysis by the tool. The tool may thus be made to conduct a specified search on an individual codebase, or to conduct a specified search on multiple selected codebases simultaneously or pseudo-simultaneously (i.e., in a time-shared fashion).

The user input interface 416 illustratively includes an on-screen "search strings" button 420 and an on-screen "exclude strings" button 430. In the screen shot illustrated in FIG. 4, the "search strings" button 420 is selected, which illustratively produces a list of selectable search strings for inclusion in the codebase search to be conducted by the impact analysis sub-module 262. In the screen shot illustrated in FIG. 4, the search string "ICD9Code" 422 is selected, which will subsequently result in a search (when selectively initiated by the user) of the selected codebase 414 for all code lines that include this term.

The user input interface 440 illustratively includes an on-screen "iteration count" selector 442 which allows the user to specify the number search iterations to be conducted. This feature allows the user to selectively conduct "deep dive" searches of the codebase in multiple iterations for variables which have been assigned values by search tokens in previous search iterations. The user input interface 440 further illustratively includes an on-screen "search" button 450 via which the user may selectively initiate a search according to the search parameters selected via the data input tab 402.

Figure 5:
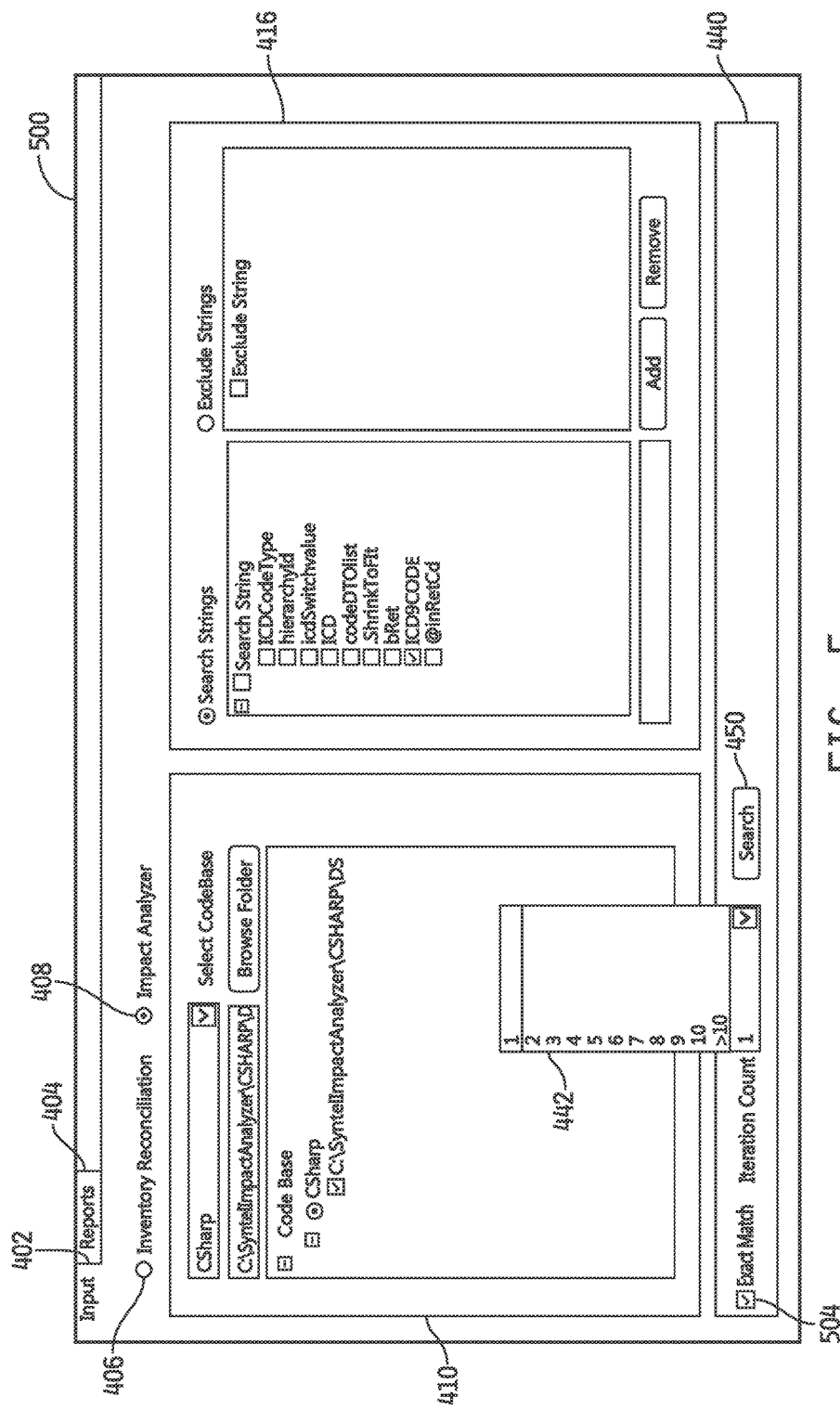
FIG. 5 is an example screen shot illustrating a process for inputting additional information into the system of FIG. 1 for processing by the impact analysis sub-module illustrated in FIG. 2.

Referring now to FIG. 5, a main menu screen 500 is shown of an alternate embodiment of the tool which illustratively includes all of the features illustrated in the main menu screen 400 illustrated in FIG. 4 and in which the user input interface 440 is replaced with an alternate user input interface 502. The user input interface 502 illustratively includes the on-screen "iteration count" selector 442 and the on-screen "search" button 450 as described above, and further illustratively includes an on-screen, selectable search matching feature 504. In the embodiment illustrated in FIG. 5, the search match feature is provided in the form of an "exact search" check box 504 which, if checked or otherwise selected by the user, will require an exact match between at least one of the selected search strings and the language recited in a line of the selected codebase for that line to be identified as an impacted code line during a subsequent user-initiated search of the codebase. If the "exact search" checkbox 504 is not checked or otherwise selected by the user, a subsequent user-initiated search of the codebase, in one embodiment, will identify as an impacted code line any code line that recites at least a portion of at least one of the selected search strings (which may be referred to herein as a "partial search"). Alternatively, an unchecked "exact search" checkbox 504 may result in the identification as an impacted code line in a subsequently initiated search any code line that recites language that is close, or perhaps closest, in meaning to, or otherwise similar in character make-up to, at least one of the selected search strings. In any embodiment, identification of an impacted code line during a user-initiated search of the codebase by anything other than an exact match with at least one search string may be referred to herein as an inexact match.

Figure 6:
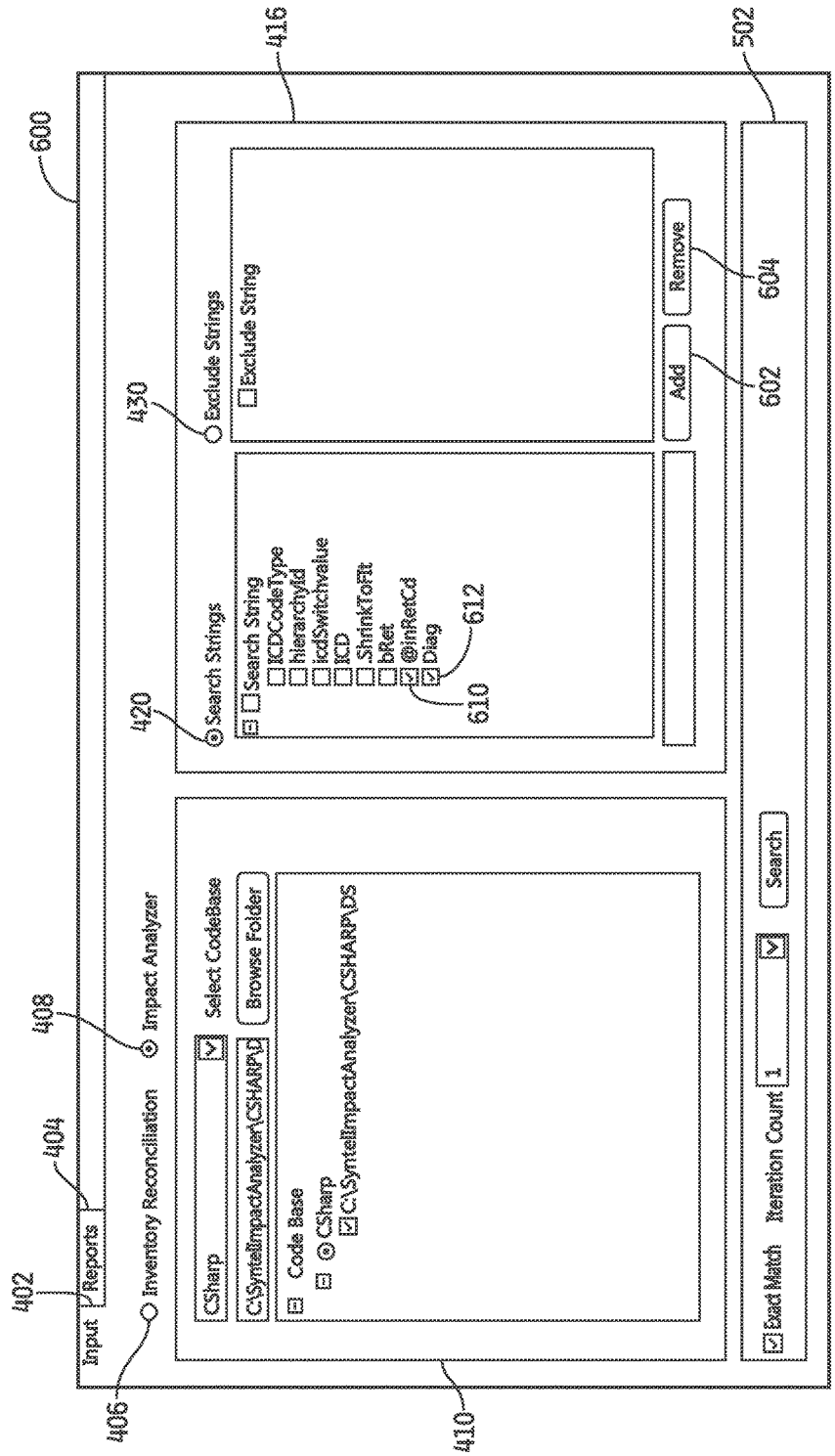
FIG. 6 is an example screen shot illustrating a process for specifying one or more search strings for processing by the impact analysis sub-module illustrated in FIG. 2.

Referring now to FIG. 6, a main menu screen 600 is shown of the tool which illustratively includes all of the features illustrated in the main menu screen 400 illustrated in FIG. 4 (optionally also including the "exact match" feature) and which illustrates the inclusion of search string add 602 and remove 604 buttons in the user input interface 416. In the illustrated embodiment, the user has employed the remove button 604 to remove "ICD9Code" from the search string options (as compared with FIG. 4), and has employed the add button 602 to add "Diag" 612 to the search string options (as also compared with FIG. 4), and has further selected "@InRetCd" 610 and "Diag" 612 to the search strings to be subsequently searched for in the selected codebase. Through the use of the add 602 and remove 604 buttons, the user may thus populate the list of available search strings with any desired one or set of search strings, and thus select any one or combination of such search strings to be subsequently searched for in the selected database.

Figure 7:
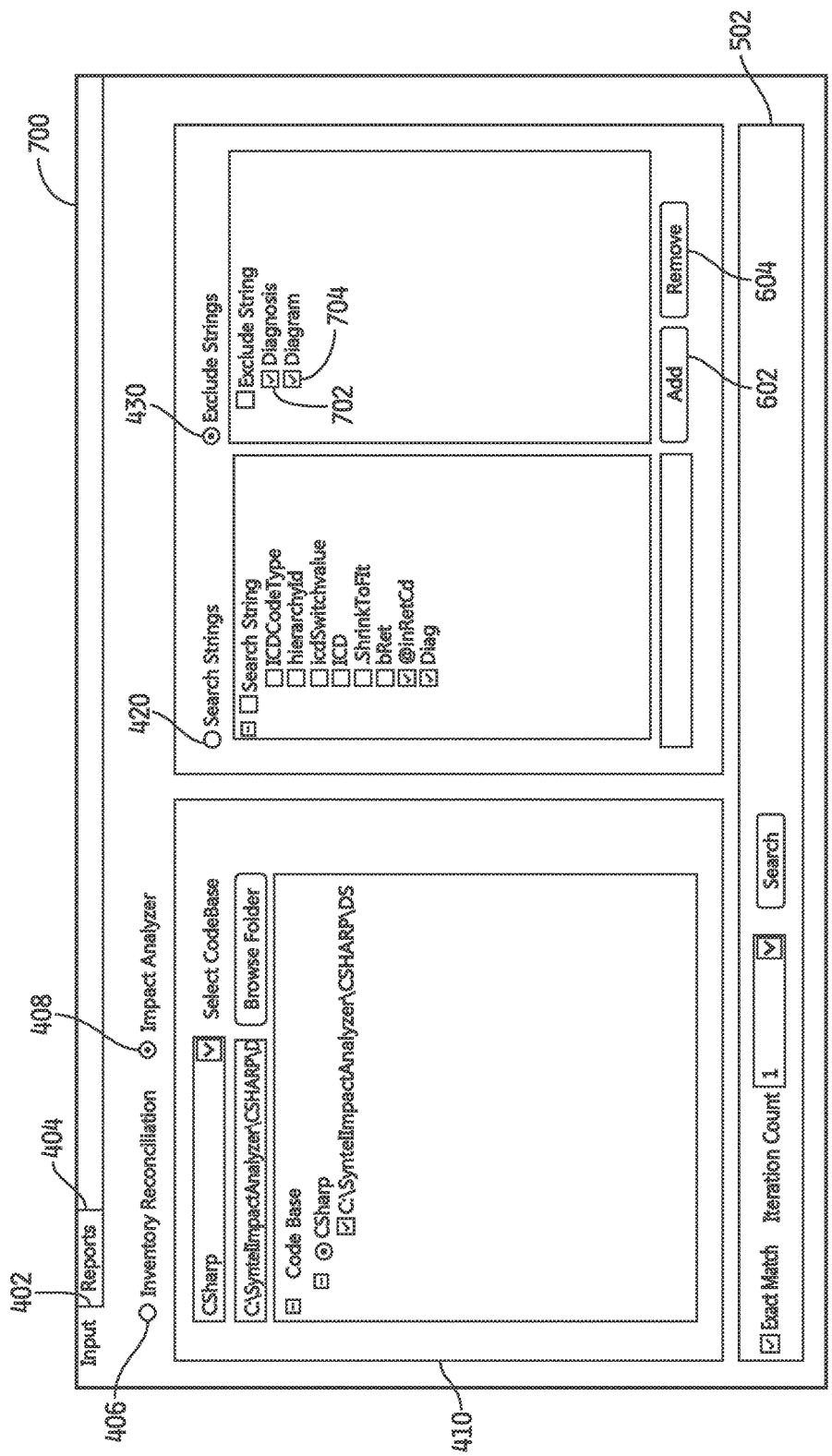
FIG. 7 is an example screen shot illustrating a process for specifying one or more search strings to be excluded during processing by the impact analysis sub-module illustrated in FIG. 2.

Referring now to FIG. 7, a main menu screen 700 is shown of the tool which illustratively includes all of the features illustrated in the main menu screen 400 illustrated in FIGS. 4 and 6 (and optionally also including the "exact match" feature of FIG. 5), and which illustrates user selection of the "exclude strings" radial button 430. The "exclude strings" feature 430 illustratively operates identically to the "search strings" feature in that the user may employ the add 602 and remove 604 buttons to populate the "exclude strings" 430 list with any one or set of search strings. User selection of any individual string in the "exclude strings" 430 list will result in exclusion of the corresponding word, number or alphanumeric code from a search of the codebase subsequently initiated by the user (via selection of the "search" button 450). In the illustrated embodiment, the user has thus elected to exclude the search terms "Diagnosis" 702 and "Diagram" 704 from a search to be subsequently conducted on the selected codebase.

Illustratively, a history (or histories) of search strings and excluded strings used in conducting codebase searches is maintained by the tool, e.g., in a file that resides at a setup executable path. Such a file may be referred to by users when conducting future searches, and/or may be used by the tool as a library of search terms from which to make recommendations to users for future searches.

Figure 8:
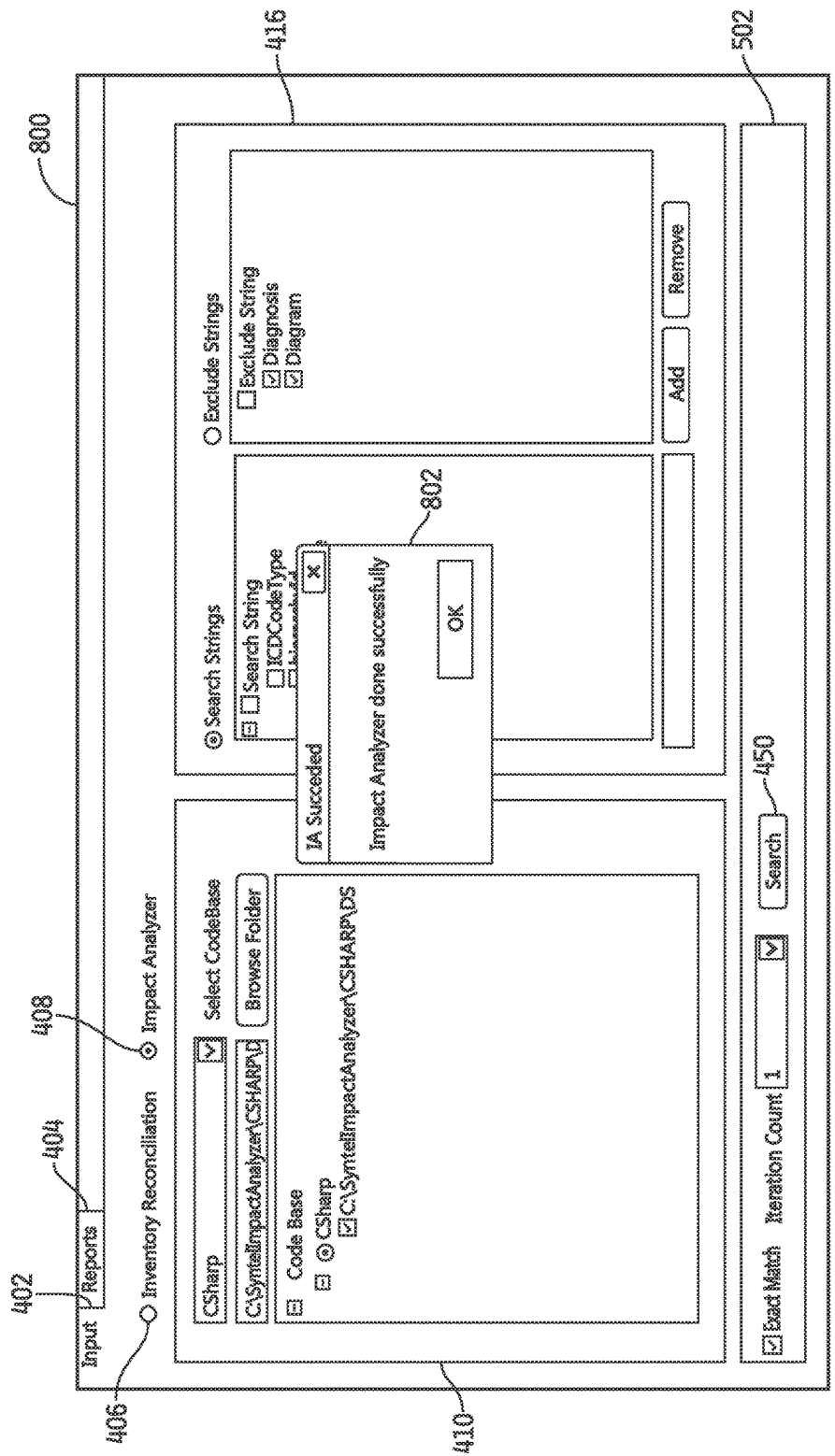
FIG. 8 is an example screen shot illustrating conclusion of a successful search conducted by the impact analysis sub-module illustrated in FIG. 2.

Referring now to FIG. 8, a main menu screen 800 is shown of the tool which illustratively includes all of the features illustrated in the main menu screen 400 illustrated in FIGS. 4 and 6-7 (and optionally also including the "exact match" feature of FIG. 5), and which illustrates a user interface produced by the tool following a successful search by the impact analysis sub-module 262 of a selected codebase using the search parameters selected by the user. In the illustrated embodiment, a graphic 802 is overlaid on the impact analysis user interface informing the user of a successful operation of the impact analysis sub-module 262.

Figure 9:
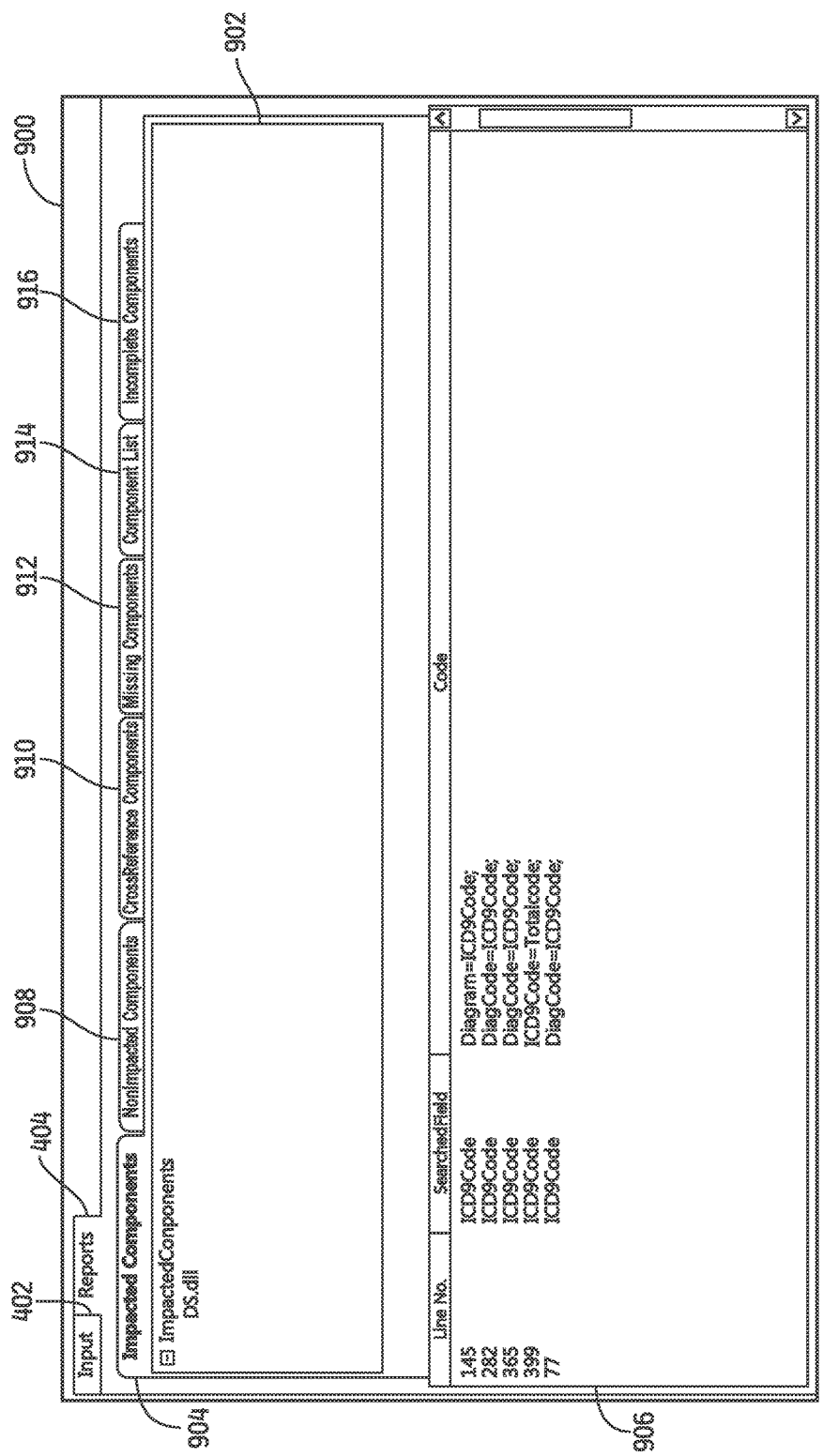
FIG. 9 is an example screen shot illustrating one type of report produced by the impact analysis sub-module illustrated in FIG. 2.

Referring now to FIG. 9, a menu screen 900 is shown of the reports tab 404 following operation of the impact analysis sub-module 602 as illustrated in FIG. 8. The reports tab 404 illustratively includes a plurality of different in-tool reports to choose from, each of which displays information that is particular to that report. In the illustrated embodiment, for example, the reports tab 404 includes an "impacted components" report 904 which is selected for display in FIG. 9. The impacted components report 904 illustratively includes a user interface 902 in which the impacted components, i.e., those components in the codebase which contain items selected in the search string 420, are listed, and a user interface 906 in which the line number, searched field and corresponding code in the identified line of the codebase is shown. In the example illustrated in FIG. 9, the sole impacted component in the selected codebase is DS.dll, and the search string "ICD9Code" was found at lines 145, 282, 365, 399 and 77 of the codebase.

Other in-tool reports available via the reports tab 404 may include, but are not limited to, a non-impacted components report 908, which is illustratively the opposite of the impacted components report 904 illustrated in FIG. 9 (i.e., which lists components in the selected codebase which do not contain any of the items selected in the search string 420), a cross-reference components report 910 which illustratively lists dependencies of search string items across components and/or component types in the codebase, a missing components report 912 which illustratively lists components in the codebase that lack definitions, a component list report 914 which illustratively lists all components in the component repository, i.e., all impacted, non-impacted, missing and incomplete components, and an incomplete components report 916 which illustratively lists components in which one or more files are missing, e.g., if the .dll is present but CSproj or VbProj files are missing in a .Net code codebase.

Figure 10:
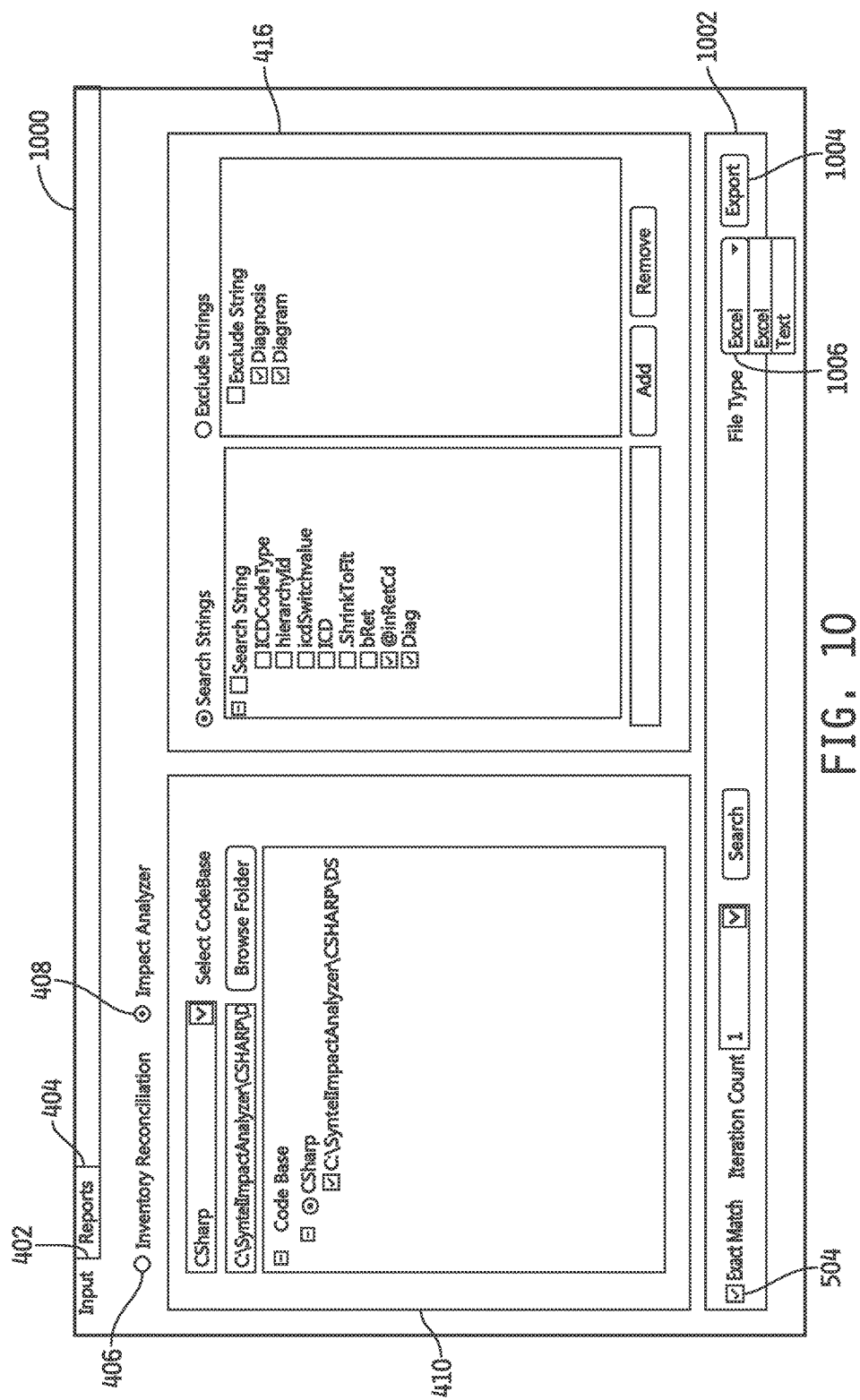
FIG. 10 is an example screen shot illustrating a report exporting feature of the impact analysis sub-module illustrated in FIG. 2.

Referring now to FIG. 10, a main menu screen 1000 is shown of an alternate embodiment of the tool which illustratively includes all of the features illustrated in the main menu screen 400 illustrated in FIGS. 4 and 6-9 (and optionally also including the "exact match" feature of FIG. 5) and in which the user input interface 440, 502 is replaced with an alternate user input interface 1002. The user input interface 1002 illustratively includes the on-screen "iteration count" selector 442 and the on-screen "search" button 450 as described above, and may optionally further include an on-screen, selectable search matching feature 504 as illustrated in FIG. 5, and in any case additionally includes a report exporting button 1004 and file type selection menu 1006. In the embodiment illustrated in FIG. 10, the report file selection menu 1006 illustratively provides for exportation of reports in Excel™ or text format, although other formats may alternatively be uses such as, but not limited to, Word™ format or other desired format. In any case, the report exporting button 1004 may be used to selectively export reports, and in some embodiments the tool exports a plurality of reports in the selected reporting format. Referring to FIG. 11, for example, an Excel™ report 1100 has been exported by the tool in response to user selection of the export button 1002. In the example illustrated in FIG. 11, the exported report illustratively includes a number of different report types each available via a different tab in the export application. For example, the exported report illustratively includes a detail report 1102, as illustrated in FIG. 11, a summary report 1104, a cross-reference report 1106 and a missing component report 1108. An instruction tab 1110 may also be included to provide user guidance, e.g., in the form of instructions, for navigating one or more of the exported reports. The detail report 1102 shown in FIG. 11 illustratively includes, e.g., arranged by columns, library name, component name, component type, file name, iteration number, line number, code, variable name, next level variable and impacted category.

Figure 12:
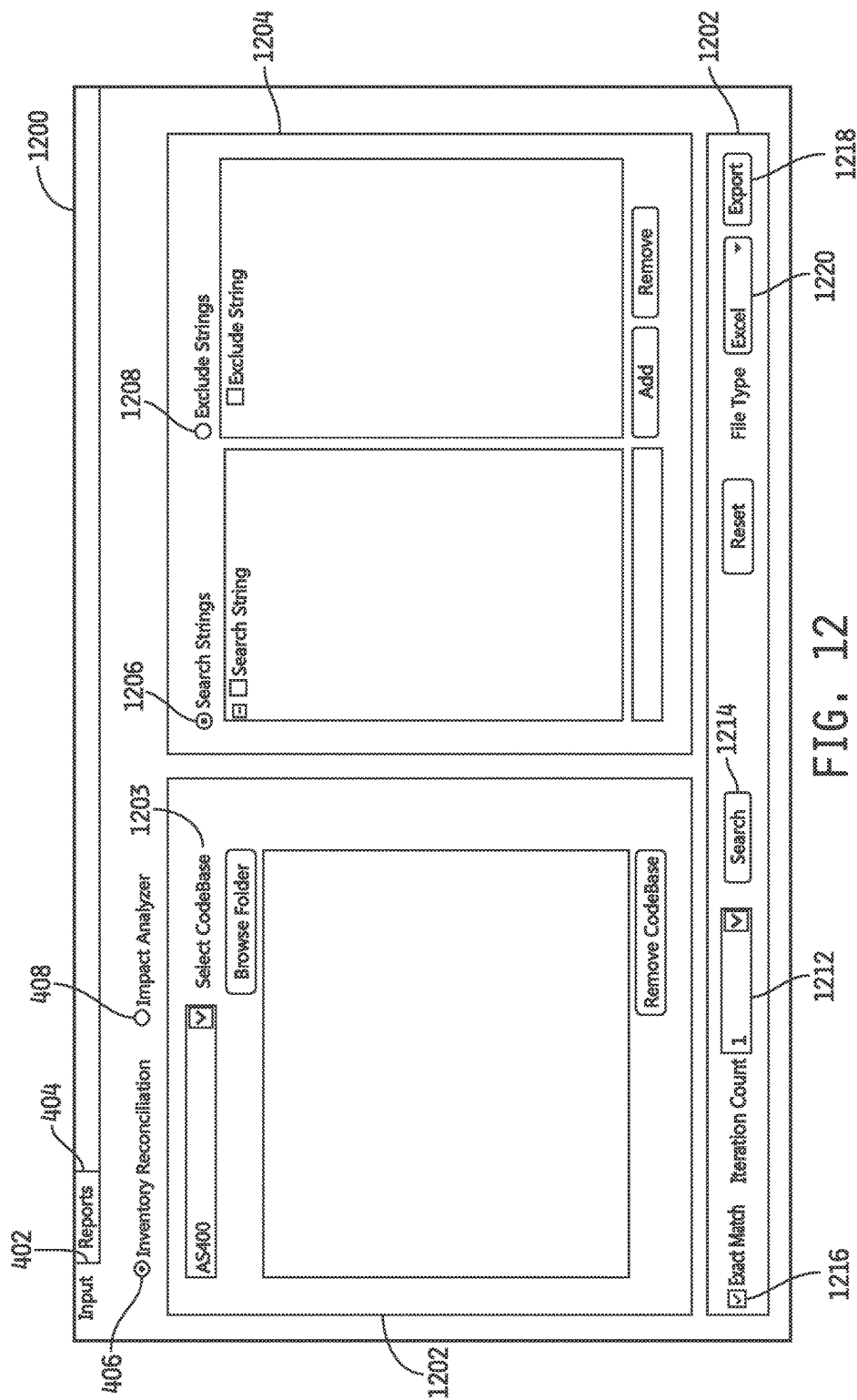
FIG. 12 is an example screen shot illustrating a process for inputting information into the system of FIG. 1 for processing by the inventory reconciliation sub-module illustrated in FIG. 2.

Referring now to FIG. 12, a main menu screen 1200 is shown of the tool which is identical to the main menu screen 400 illustrated in FIG. 4, but in which the user has selected the inventory reconciliation radio button 406 and the data input tab 402. In response, the tool produces a set of user interfaces 1202, 1204 and 1210 each of which are illustratively substantially identical to the user interfaces 410, 416 and 440 respectively illustrated in FIG. 4. For example, the user interface 1202 illustratively includes a codebase selection button 1203 that may be selected by the user to load one or more codebases for analysis by the inventory reconciliation sub-module 264. The search string 1206 and exclude strings 1208 selection features, including features for adding and removing either such strings within user interface 1204 will be disabled for the inventory reconciliation radio button 406 selection. The user interface 1210 illustratively includes a search button 1214 and a report exporting button 1218 and corresponding report file format menu 1220, all a described hereinabove with respect to FIG. 4. The iteration count menu 1212 and exact match selection feature 1216 within user interface 1210 will be disabled for the inventory reconciliation radio button 406 selection.

Figure 13:
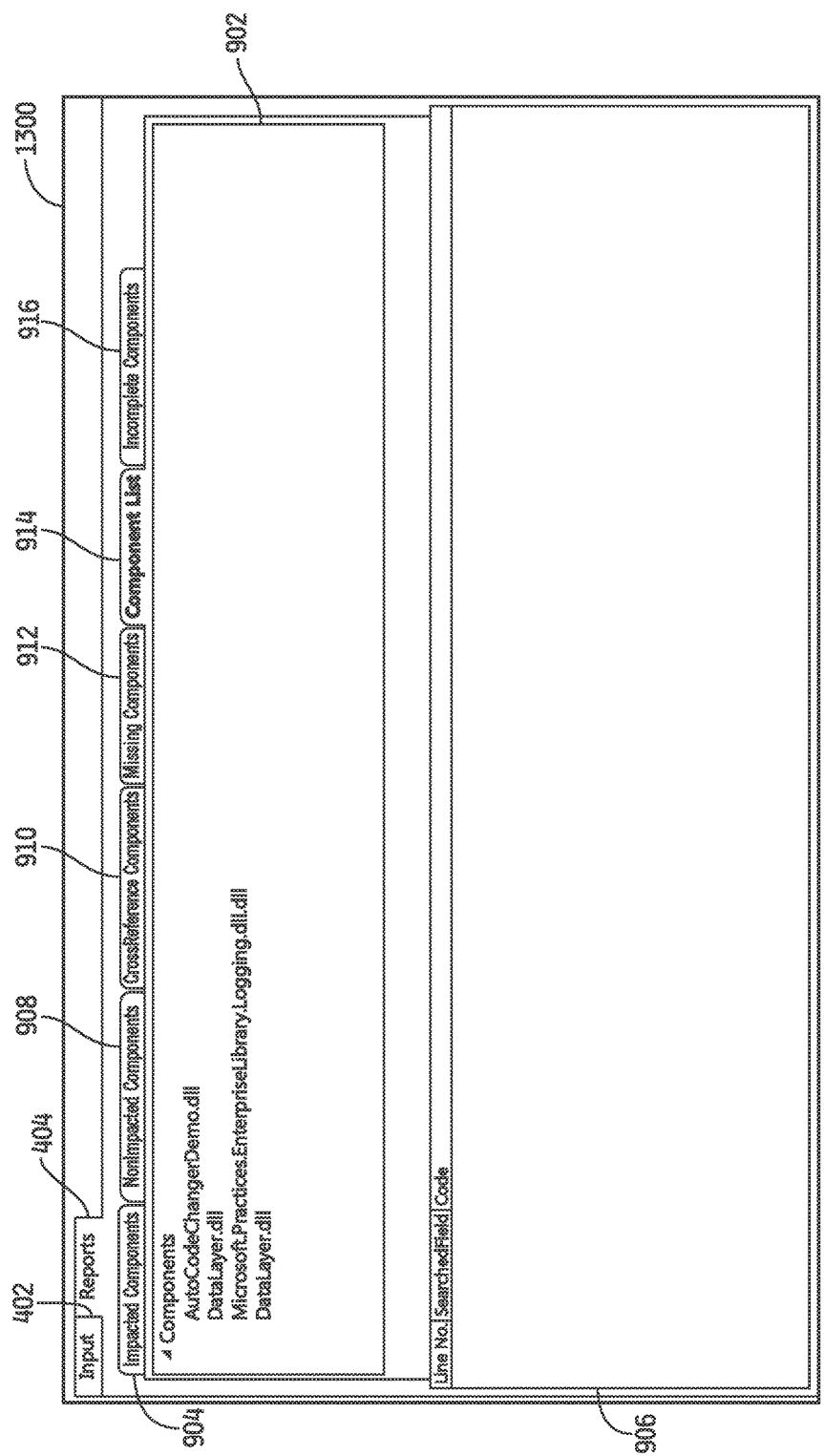
FIG. 13 is an example screen shot illustrating one type of report produced by the inventory reconciliation sub-module illustrated in FIG. 2.

Referring now to FIG. 13, a screen 1300 is shown as produced by the tool in response to selection of the reports tab 404 when the inventory reconciliation button 408 is selected. The reports tab 404 illustrated in FIG. 13 includes user interfaces 902 and 906 which are illustratively identical to like-numbered user interfaces illustrated and described with respect to FIG. 9, and within the user interface 904 a number of different reports are available including, for example, but not limited to, a cross-reference components report 910, a missing components report 912, a component list report 914 and an incomplete components report 916, all as described hereinabove with respect to FIG. 9. The impacted components report 904 and non-impacted components report 908 will not be generated for inventory reconciliation.

Operation of the inventory reconciliation sub-module 264 differs from operation of the impact analysis sub-module 262 in one sense in that the former identifies and collects a list of all the impacted components and missing/incomplete components in a codebase, whereas the latter identifies and collects all impacted lines of source code in a codebase. When migrating from ICD-9 to ICD-10, the impact analysis module 262 may be used to identify those impacted lines of source code in the codebase that will require modification in order to support an ICD-10 code set, and the inventory reconciliation sub-module 264 may be used to identify all impacted components in a codebase, all missing components and incomplete components, as well as their component types. For example, prior to analyzing any codebase in relation to the impending ICD-9 to ICD-10 migration, it may be desirable to verify and reconcile software applications that are within the scope of the ICD-10 migration; i.e., that include impacted components. This process of "taking stock" of a customer's applications may be performed by the inventory reconciliation module.

For example, the components can have logical, temporal, and other types of dependencies among the components that form the systems. For a given component to complete a task from start to end it may need to call upon other components, or chains of components, in order to perform required processing; or the given component may require information or data from one or more other components or a chain of components for completion of the task. Large, complex chains of such dependencies can develop, especially as a system increases in size and complexity. Accordingly, the inventory reconciliation module creates a cross reference report that captures these dependencies across components.

In some instances, components may be modified (definition altered), moved, or otherwise missing. The inventory reconciliation module also create a report that shows a list of these missing components. In some other instances, components may indeed be present; however, associated project files may be missing. Accordingly, the tool creates an "incomplete report" listing these components. Another report created by the inventory reconciliation module is a component list report, which is simply a listing of all components including impacted, non-impacted, missing, incomplete components, and the like. Thus, the impact analysis sub-module 262 operates to identify and collect all impacted lines of code in a codebase based on one or more specified search strings, and the inventory reconciliation sub-module 264 operates to identify and collect all impacted components in a codebase based on one or more specified search strings.

While the disclosure has been illustrated and described in detail in the drawings and foregoing description, such an illustration and description is to be considered as exemplary and not restrictive in character, it being understood that only illustrative embodiments have been shown and described and that all changes and modifications consistent with the disclosure and recited claims are desired to be protected.

What is claimed is:

1. A system for analyzing an impact of a software migration on a codebase, comprising:
   a memory storing:
   a data management module to receive user-selected input of the codebase that supports international classification of diseases, ninth revision (ICD-9) codes and that contains a plurality of codebase components, the codebase components including source code of a unit of a computer software program, file/table definition and job controlling language/procedure;
   a codebase analysis module to analyze the codebase to identify each impacted codebase component requiring modification in order to support migration from ICD-9 codes to international classification of diseases, tenth revision (ICD-10) codes and to determine dependencies of each impacted codebase component requiring modification on other codebase components, and to analyze the codebase using the at least one search string to identify each impacted line of source code requiring modification in order to support migration from ICD-9 code to international classification of diseases, tenth revision (ICD-10) codes; and
a report module to produce at least one report of a result of the analysis of the codebase by the codebase analysis module, wherein the report module is configured to produce the at least one report, the at least one report including a listing of each impacted codebase component and a listing of dependencies of each impacted codebase component.

2. The system of claim 1, wherein the memory further stores a user interface module to produce at least one graphic user interface for receiving user input of the codebase, and wherein the source code includes a plurality of computer programming languages.

3. The system of claim 1, wherein the memory further stores a user interface module to produce at least one graphic user interface for receiving user selection to export the at least one report in a selected report file format, and wherein the report module is configured to export the at least one report to a report file having the selected report file format.

4. The system of claim 1, wherein the codebase analysis module is further configured to determine missing codebase components and incomplete codebase components.

5. The system of claim 1, wherein the at least one report includes an impacted components report, a cross-reference components report, a missing components report, a component list report, and an incomplete components report.

6. A computer program product comprising non-transitory computer readable medium having instructions stored thereon which, when executed by at least one processor, cause the processor to:
receive user-selected input of a codebase that supports international classification of diseases, ninth revision (ICD-9) codes and that contains a plurality of lines of source code and a plurality of codebase components including source code of a unit of a computer software program, file/table definition and job controlling language/procedure,
receive user selection of an analysis initiation,
in response to receipt of the analysis initiation, analyze the codebase to identify each impacted codebase component requiring modification in order to support migration from ICD-9 codes to international classification of diseases, tenth revision (ICD-10) codes, and to determine dependencies of each impacted codebase component requiring modification on other components, and to analyze the codebase using the at least one search string to identify each impacted line of source code requiring modification in order to support migration from ICD-9 code to international classification of diseases, tenth revision (ICD-10) codes; and
produce at least one report of a result of the analysis of the codebase, wherein the report module is configured to produce the at least one report, the at least one report including a listing of each impacted codebase component and a listing of dependencies of each impacted codebase component.

7. The computer program product of claim 6, wherein the instructions stored on the computer readable medium further include instructions which, when executed by the at least one processor, cause the processor to determine missing codebase components.

8. The computer program product of claim 6, wherein the instructions stored on the computer readable medium further include instructions which, when executed by the at least one processor, cause the processor to determine incomplete codebase components.

9. In a computer, having at least one processor and a memory for storing instructions executable by the at least one processor for analyzing an impact of a software migration on a codebase, the instructions comprising:
receiving, by a data management module, a user-selected input of the codebase that supports international classification of diseases, ninth revision (ICD-9) codes and that contains source code of a unit of a computer software program, file/table definition and job controlling language/procedure;
analyzing, by a codebase analysis module, the codebase using the at least one search string to identify each impacted line of source code requiring modification in order to support migration from ICD-9 codes to international classification of diseases, tenth revision (ICD-10) codes, and to analyze the codebase using the at least one search string to identify each impacted line of source code requiring modification in order to support migration from ICD-9 code to international classification of diseases, tenth revision (ICD-10) codes; and
producing, by a report module, at least one report of a result of the analysis of the codebase by the codebase analysis module, wherein the report module is configured to produce the at least one report, the at least one report including a listing of each impacted codebase component and a listing of dependencies of each impacted codebase component.

10. The system of claim 9, wherein the memory further stores a user interface module to produce at least one graphic user interface for receiving user input of the codebase and the at least one search string.

11. The system of claim 9, wherein the data management module is configured to receive user-selected input of at least one excluded string, and
wherein the codebase analysis module is configured to analyze the codebase by searching the codebase for matches with the at least one search string and excluding matches with the at least one excluded string.

12. The system of claim 9, wherein the data management module is configured to receive user-selected input of an iteration count, and wherein the codebase analysis module is configured to analyze the codebase by searching the codebase for matches with a respective search string for each of a number of times specified by the iteration count.

13. The system of claim 9, wherein the data management module is configured to receive user-selected of an exact match requirement, and
wherein the codebase analysis module is configured to analyze the codebase by searching the codebase for exact matches with the at least one search string.

14. The system of claim 13, wherein the codebase analysis module is configured to analyze the codebase by searching the codebase for inexact matches with the at least one search string in the absence of user selection of the exact match requirement.

15. The system of claim 9, wherein the codebase analysis module is further configured to identify each impacted codebase component requiring modification in order to support migration from ICD-9 codes to ICD-10 codes.

16. The system of claim 15, wherein the codebase analysis module is further configured to determine dependencies of each impacted codebase component requiring modification on other components.

17. The system of claim 9, wherein the report module is configured to produce the at least one report, the at least one report includes an impacted components report, a cross-reference components report, a missing components report, a component list report, and an incomplete components report.

* * * * *